United States Patent [19]

Tobutt

[11] Patent Number: Plant 6,184

[45] Date of Patent: May 24, 1988

[54] COLUMNAR APPLE TREE—MAYPOLE VARIETY

[75] Inventor: Kenneth R. Tobutt, Kent, England

[73] Assignees: The Kent Incorporated Society for Promoting Experiments in Horticulture, Kent; National Seed Development Organisation Limited, Cambridge, both of England

[21] Appl. No.: 852,341

[22] Filed: Apr. 15, 1986

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

A new and distinct variety of ornamental crab apple tree is provided which exhibits an extremely columnar growth habit which generally resembles that of a vertical pole. The foliage is dense and compact and side branches are substantially absent. The new variety yields attractive crimson fruit which is suitable for making jelly. The young leaves are purple tinted.

1 Drawing Sheet

SUMMARY OF THE INVENTION

The new variety of apple tree was created in the course of a plant breeding program which was initiated during 1976 at the East Malling Research Station of The Kent Incorporated Society for Promoting Experiments in Horticulture at East Malling, Maidstone, Kent, England. The parents of the new variety were the Wijcik variety (U.S. Plant Pat. No. 4,382) of McIntosh apple tree, and Malus Baskatong. This parentage can be summarized as follows:

Wijcik × Malus Baskatong.

Approximately 100 crosses were made between the respective parents. Approximately 20 fruits were formed which contained five viable seeds each. Approximately 100 seedlings were formed from the germination of such seeds and the resulting trees were subjected to detailed study. A single plant of the new variety was selected. During the selection process the absence of side branches was a major factor.

It was found that the new variety of ornamental apple tree of the present invention possesses the following combination of characteristics:

(a) an erect, dense and compact growth habit which is substantially free of side branches, and
(b) the ability to form attractive small symmetric crimson fruit.

The extremely columnar nature of the new variety is particularly striking. Side branches are very limited and tend to form only when the terminal bud is damaged (e.g., by mildew, etc.). When side branches occur, they can be easily removed with secateurs. The axillary buds tend to form fruit-producing spurs rather than extension shoots. The foliage is dense and compact and the internodes are short. The flowers and fruit tend to form along a single main stem or trunk which gives the entire tree the appearance of a vertical pole. The trees commonly grow in height at a rate of approximately 1.5 feet per season.

The new variety forms purple tinted young leaves, carmine flowers, and crimson fruit suitable for making jelly.

The distinctive growth habit of the new variety makes possible the extremely dense planting of the new variety if desired. For instance, the new variety can be grown in a row with the trees being spaced approximately 1 yard apart. A row of trees of the new variety forms a sturdy natural ornamental cordon. However, in extremely windy areas it may be desirable to at least partially shelter the trees from the wind with appropriate wind barriers. Extreme wind exposure may undesirably result in the destruction of the terminal bud and thereby tend to promote secondary branching. The trees of the new variety are relatively easy to manage and require little pruning. Mechanized picking readily can be implemented if desired. The trees can well be used for ornamental purposes in gardens, parks, and along roadsides. Additionally, the trees of the new variety can serve as space-saving pollinators in more conventional orchards.

The new variety has been found to undergo asexual propagation by a number of routes, including budding, grafting, etc. The characteristics of the new variety have been found to be strictly transmissible by such asexual propagation from one generation to another.

The new variety performs well on dwarfing rootstocks, such as MM 106, and it is not recommended that it be grown on its own roots. Also, it has performed well at the 1984 National Fruit Trials, Brogdale Farm, Faversham, Kent, England.

Initially, the new variety was designated SA 244-20, and subsequently has been named the Maypole variety.

BRIEF DESCRIPTION OF THE PHOTOGRAPH

The accompanying photograph shows as nearly true as it is reasonably possible to make the same, in a color illustration of this character, typical specimens of the new variety.

FIG. 1 illustrates a section of the vertical trunk of the new variety showing the abundant production of attractive crimson fruit.

DETAILED DESCRIPTION

Figure 1:
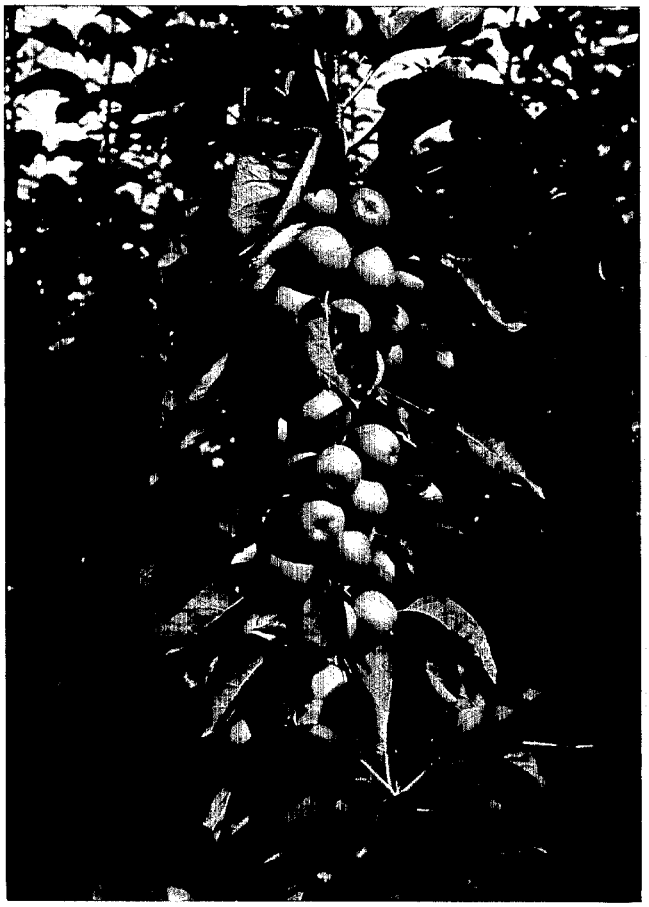

The specimens described were grown at the Brogdale Experimental Horticulture Station, Faversham, Kent, England.

Tree:

*Habit of branches.*—A conventional branching system along the tree trunk is lacking, branches rarely form when the terminal bud is undamaged.

*Growth habit.*—Compact and dense with short internodes.

*Vigor.*—Weak.

*Dormant one year old shoot.*—Pubescence is present in a moderate amount, thin leader thickness, and a moderate quantity of lenticels.

Leaves:

*Leaf configuration.*—Elongated as illustrated, commonly having a length : width ratio of approximately 1.7.

*Leaf margin.*—Crennate, sometimes bicrennate.

*Leaf appearance.*—Medium glossy, purple-tinted when young.

*Petiole.*—Long, approximately 44.5 mm. in length on average.

*Leaf posture.*—Generally outwards.

Flowers:

*Dormant bud shape.*—Ovoid.

*Bud pubescence.*—Medium.

*Bud color.*—Red-Purple Group 63A of The R.H.S. Colour Chart.

*Beginning of flowering.*—Approximately 4 days earlier than Cox's Orange Pippin when 10 percent flowering occurs.

*Flower shape.*—Moderately cupped.

*Flower size.*—Medium.

*Flower color.*—Red-Purple Group 63A of The R.H.S. Colour Chart.

*Sepals.*—Predominantly red in coloration.

*Petal shape.*—Longer than broad, have a length : breadth ratio of approximately 1.3 to 1.4 on average.

*Relation of petal margins.*—Slightly overlapping.

*Styles.*—Substantially the same length as the stamens, attached away from the base.

Fruit:

*Predominance of bearing.*—On spurs.

*Size.*—Very small, approximately 36 mm. on average.

*Shape.*—Round-conical.

*Symmetry in sideview.*—Symmetric.

*Ribbing.*—Absent.

*Crowning at distal end.*—Present and not prominent.

*Aperture of eye.*—Closed.

*Size of eye.*—Small (calyx often abscissed).

*Length of sepal.*—Short.

*Attitude of sepal.*—Convergent when present.

*Spacing of sepals at base.*—Not easily observable.

*Ribbing of basin.*—Absent.

*Protrusion of stalk.*—Much beyond cavity.

*Thickness of stalk.*—Thin.

*Length of stalk.*—Very long.

*Stalk cavity depth.*—Medium.

*Surface texture of skin.*—Smooth.

*Bloom of skin.*—Present.

*Greasiness of skin.*—Present in a substantial quantity.

*Cracking tendency of skin.*—Absent.

*Skin color.*—Crimson red (garnet brown 00918/1 with reference to The R.H.S. Horticultural Chart — Page 192). The coloration is present as a solid flush.

*Russet.*—Absent.

*Lenticels.*—Small in size.

*Browning of flesh.*—Strong.

*Color flesh.*—Pink.

*Cavity beneath eye.*—U or V-shaped when examined in longitudinal section.

*Position of stamens.*—Marginal when examined in longitudinal section.

*Shape of core.*—Symmetric when examined in longitudinal section.

*Color of core.*—Deep pink.

*Distinctness of coreline.*—Very strong when examined in cross-section.

*Aperture of cells.*—Open when examined in cross-section.

*Color of fresh seed.*—Red brown.

I claim:

1. A new and distinct variety of ornamental apple tree, substantially as illustrated and described, having (a) an erect, dense and compact growth habit which is substantially free of side branches, and (b) the ability to form attractive small symmetrical crimson fruit.

* * * * *